US012083516B2

United States Patent
Du et al.

(10) Patent No.: US 12,083,516 B2
(45) Date of Patent: Sep. 10, 2024

(54) PORTABLE ELECTRICAL IMPEDANCE-BASED BLOOD TESTING DEVICE FOR DIAGNOSIS AND MONITORING SICKLE CELL DISEASE

(71) Applicant: FLORIDA ATLANTIC UNIVERSITY BOARD OF TRUSTEES, Boca Raton, FL (US)

(72) Inventors: E Du, Boca Raton, FL (US); Darryl Dieujuste, Boca Raton, FL (US); Jia Liu, Boca Raton, FL (US); Yuhao Qiang, Boca Raton, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 0 days.

(21) Appl. No.: 18/118,279

(22) Filed: Mar. 7, 2023

(65) Prior Publication Data

US 2023/0211340 A1    Jul. 6, 2023

Related U.S. Application Data

(62) Division of application No. 16/585,897, filed on Sep. 27, 2019, now Pat. No. 11,618,019.

(Continued)

(51) Int. Cl.
*B01L 3/00*  (2006.01)
*G01N 15/10*  (2024.01)
(Continued)

(52) U.S. Cl.
CPC ... *B01L 3/502715* (2013.01); *B01L 3/502761* (2013.01); *G01N 15/1031* (2013.01);
(Continued)

(58) Field of Classification Search
CPC ........ B01L 3/502715; B01L 3/502761; B01L 2300/025; B01L 2300/06;
(Continued)

(56) References Cited

U.S. PATENT DOCUMENTS

2012/0258488 A1*  10/2012  Abilez ............... C12M 47/04
                                                            435/287.1
2016/0238553 A1*  8/2016  Shachar ............ G01N 27/4145
2018/0267021 A1   9/2018  Suresh et al.

OTHER PUBLICATIONS

Data & Statistics on Sickle Cell Disease, Centers for Disease Control and Prevention, 2017.

(Continued)

*Primary Examiner* — Dean Kwak
(74) *Attorney, Agent, or Firm* — Meunier Carlin & Curfman LLC

(57) ABSTRACT

An exemplary mobile impedance-based flow cytometer is developed for the diagnosis of sickle cell disease. The mobile cytometer may be controlled by a computer (e.g., smartphone) application. Calibration of the portable device may be performed using a component of known impedance value. With the developed portable flow cytometer, analysis may be performed on two sickle cell samples and a healthy cell sample. The acquired results may subsequently be analyzed to extract single-cell level impedance information as well as statistics of different cell conditions. Significant differences in cell impedance signals may be observed between sickle cells and normal cells, as well as between sickle cells under hypoxia and normoxia conditions.

8 Claims, 9 Drawing Sheets

Related U.S. Application Data

(60) Provisional application No. 62/773,677, filed on Nov. 30, 2018.

(51) Int. Cl.
  *G01N 15/1031* (2024.01)
  *G01N 15/14* (2024.01)
  *G01N 15/1429* (2024.01)
  *G01N 33/49* (2006.01)
  *G01N 15/01* (2024.01)

(52) U.S. Cl.
  CPC .... *G01N 33/4915* (2013.01); *B01L 2300/025* (2013.01); *B01L 2300/06* (2013.01); *B01L 2300/0645* (2013.01); *B01L 2300/0809* (2013.01); *B01L 2300/16* (2013.01); *G01N 2015/012* (2024.01); *G01N 2015/1006* (2013.01); *G01N 15/1425* (2013.01); *G01N 15/1431* (2013.01); *G01N 15/1484* (2013.01)

(58) Field of Classification Search
  CPC ..... B01L 2300/0645; B01L 2300/0809; B01L 2300/16; G01N 15/1031; G01N 33/4915; G01N 2015/012; G01N 15/1425; G01N 15/1431; G01N 15/1484; G01N 2015/1006; G01N 15/1023
  See application file for complete search history.

(56) References Cited

OTHER PUBLICATIONS

Piel et al., "Sickle Cell Disease", The New England Journal of Medicine, vol. 376, No. 16, pp. 1561-1573, Apr. 20, 2017.
Van Beers et al., "Imaging Flow Cytometry for Automated Detection of Hypoxia-Induced Erythrocyte Shape Change in Sickle Cell Disease", American Journal of Hematology, vol. 89, No. 6, pp. 598-603, Jun. 6, 2014.
Christoph et al., "Understanding the Shape of Sickled Red Cells", Biophysical Journal, vol. 88, No. 2, pp. 371-1376, Feb. 2005.
Shapiro, H. M., "Practical Flow Cytometry", New York, A.R. Liss, 1988.
Sun et al., "Single-Cell Microfluidic Impedance Cytometry: A Review", Microfluid Nanofluid, vol. 8, No. 4, pp. 423-443, 2010.
Joo et al., "A Portable Microfluidic Flow Cytometer Based on Simultaneous Detection of Impedance and fluorescence" Biosensors and Bioelectronics, vol. 25, pp. 1509-1515, 2010.
Rottigni et al., "Handheld Bio-Impedance Measurement System Based on an Instrument-on-Chip", IEEE, 2011 7th Conference on on Ph.D. Research in Microelectronics and Electronics, pp. 49-52.
1 MSPS, 12-Bit Impedance Converter, Network Analyzer, Analog Devices, Data Sheet AD5933, http://www.analog.com/media/en/technical-documentation/data-sheets/AD5933.pdf, 2005.
Simic, M., "Realization of Complex Impedance Measurement System Based on the Integrated Circuit A5933", 21st Welecommunications Forum Telfor 2013, pp. 573-576.
Breniuc et al., Wearable Impedance Analyzer Based on AD5933, 2014 International Conference and Exposition on Electrical and Power Engineering, Oct. 16-18, 2014.
Al-Ali et al.. "Design of a Portable Low-Cost Impedance Analyzer", Proceedings of the 10th International Joint Conference on Biomedical Engineering Systems and Technologies (BIOSTEC 2017), pp. 104-109, 2017.
Talukder et al., "A Portable Battery Powered Microfluidic Impedance Cytometer With Smartphone Readout: Towards Personal Health Monitoring", Biomed Microdevices, vol. 19., No. 2, pp. 36, 2017.
Liu et al., "Electrical Impedance Microflow Cytometry With Oxygen Control for Detection of Sickle Cells", Sensors and Actuators B: Chemical, vol. 255, pp. 2392-2398, 2018.
Installing Additional Arduino Libraries, 2017.
Usach, M., "How to Configure the AD5933/AD5934", Analog Devices, http://www.analog.com/media/en/technical-documentation/application-notes/AN-1252.pdf. 2013.
GaAs MMIC SP3T Non-Reflective Switch, DC-3.5 GHZ, Analog Devices, accessed on Feb. 23, 2018 from rittp:/lwww.analog.com/media/en/technical-documentation/data-sheets/hmc245a.pdf.
Distribution Dashboard, 2018.
Product Data Sheet, Module Data Sheet, HC-06, Guangzhou HC Information Technology Co., accessed on Apr. 6, 2018 from https://www.olimex.com/Products/Components/RF/BLUETOOTH-SERIAL-HC-06/resources/hc06.pdf.
Xia et al., "Soft Lithography", Angewandte Chemie International Edition, vol. 37, No. 5, pp. 550-575, 1998.
Liu et al., "Electrical Impedance Characterization of Erythrocyte Response to Cyclic Hypoxia in Sickle Cell Disease", American Chemical Society, vol. 4, pp. 1783-1790, 2019.
CRII: SCH: A Smart Biosensorfor Monitoring Cell Sickling in Patients with Sickle Cell Disease, National Science Foundation, Award Abstract #1464102, 2015.

* cited by examiner

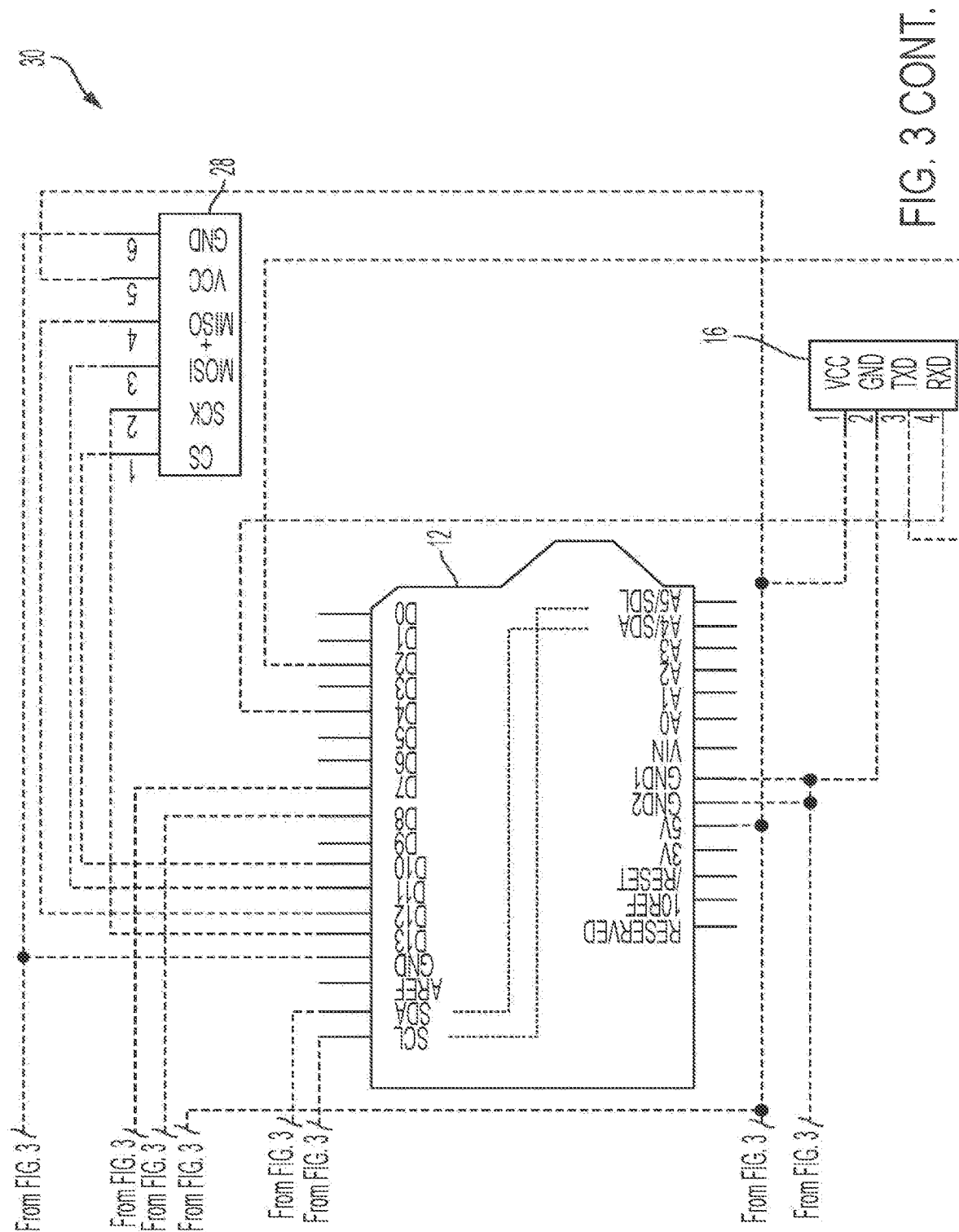

PORTABLE ELECTRICAL IMPEDANCE-BASED BLOOD TESTING DEVICE FOR DIAGNOSIS AND MONITORING SICKLE CELL DISEASE

CROSS-REFERENCE TO RELATED APPLICATIONS

This application is a divisional of U.S. Non-Provisional patent application Ser. No. 16/585,897 filed on Sep. 27, 2019 entitled Portable Electrical Impedance-Based Blood Testing Device for Diagnosis and Monitoring Sickle Cell Disease, which claims the benefit under 35 U.S.C. § 119(e) of Application Ser. No. 62/773,677 filed on Nov. 30, 2018 entitled Portable Electrical Impedance-Based Blood Testing Device for Diagnosis and Monitoring Sickle Cell Disease, the contents of which are incorporated by reference herein in their entirety.

STATEMENT REGARDING FEDERALLY SPONSORED RESEARCH OR DEVELOPMENT

This invention(s) was made with government support under grant number 1464102 awarded by the National Science Foundation. The government has certain rights in the invention(s).

FIELD OF DISCLOSURE

The disclosure relates generally to flow cytometers. More particularly, the present invention relates to portable flow cytometers that sense electrical impedance of microscopic biological particles in a flow stream. When no flow is applied, this portable flow cytometer may provide electrical impedance measurement of single biological particle or a particle suspension in a stationary condition.

BACKGROUND

Sickle cell disease is an inherited blood cell disorder that affects about 100,000 people in the US and results in high cost of medical care exceeding $1.1 billion annually. Worldwide, an estimated 300,000 infants are born with sickle cell anemia. It is an inherited blood cell disorder involving the mutation of Hemoglobin S (Hgb S) in red blood cells, which leads to formations of rigid fibers and a sickled shape as the Hgb S polymerize in low oxygen conditions. Sickle cell patients suffer from unpredictable, painful vaso-occlusive crises; in particular, the blocking of small blood vessels. This results in severe pain or organ failure for the patient.

Known diagnostic methods for sickle cell disease include premarital, antenatal and neonatal screenings for infants and hemoglobin tests for adults. Effective treatments include penicillin prophylaxis for children and hydroxyurea for all ages. The disease may be cured using hematopoietic stem cell transplantation, but the high cost leaves few able to afford the procedure. Active monitoring of the disease's severity is not possible by commercial products at this time. This leaves patients, diagnosed or not, at risk.

High throughput impedance measurement on blood cells can be done with benchtop equipment, which is non-portable, expensive and requires technical training. Currently there is no portable field sensor available to quantitatively measure and monitor cell sickling events in sickle cell disease from a low sample volume (e.g., a finger prick).

To briefly explain what impedance is, it is best to first explain Ohm's Law. Ohm's Law represents the foundation of direct current (DC) electrical signals:

$$V = I \cdot R \quad \#(1)$$

In this equation, V, I, and R, are variables for voltage, current, and resistance, respectively. This formula can be extended to alternating current (AC) circuits by replacing resistance, R, with impedance, Z. AC signals are normally expressed as sinusoids. Sinusoidal signals have three main components of interest: a magnitude, a phase, and a frequency. Magnitude can be described as the strength of the signal and phase can be described as a signal's position relative to another signal. Magnitude is measured in volts and phase is measured in degrees. Signals can be expressed in a polar form as Magnitude∠Phase or as a sum of real and imaginary components, a+jb. The two forms are interchangeable using the following equations.

$$\text{Magnitude} = \sqrt{a^2 + b^2} \quad \#(2)$$

$$\text{Phase} = \tan^{-1}\left(\frac{b}{a}\right) \quad \#(3)$$

Ohm's Law, when using AC signals, is shown in the following equation.

$$V_{mag}\angle\theta_v = (I_{mag}\angle\theta_1) \cdot (Z_{mag}\angle\theta_z) \quad \#(4)$$

Resistance is replaced by its complex counterpart, impedance. Solving for the impedance, Z, gives us the impedance equation.

$$Z_{mag}\angle\theta_Z = \frac{(V_{mag}\angle\theta_v)}{(I_{mag}\angle\theta_I)} \quad \#(5)$$

The inverse of impedance, admittance (Y) is defined as followed, $$Y = \frac{1}{Z} \quad \#(6)$$

Cytometry is the measurement of cells and other biological particles while flow cytometry incorporates the cells or particles moving in a single file in a fluid stream. Applications of flow cytometry generally include, but are not limited to, the measurements of cell size, cell shape, and the quantity of cells in a given volume. Electronic and optical measurements are the most commonly used detection methods in flow cytometry.

As can be seen in FIG. 1, a biological cell can be modeled by an equivalent circuit that consists of a capacitor as the cell membrane and a resistor as the cell's cytoplasm, as shown in FIG. 1 $C_{mem}$ is the membrane capacitance, $R_i$ is the resistance of the internal cytoplasm, $C_m$ and $R_m$ characterize the surrounding medium.

Impedance based flow cytometry is capable of providing information regarding individual particles by measuring changes in the impedance values created by particles passing through measurement electrodes. Such impedance changes can be used to characterize the biophysical properties of individual particles. The cost and size of equipment used for impedance-based flow cytometry can be excessive depending on the specific applications. It would be beneficial to provide portable alternatives, including a portable impedance-based flow cytometer.

SUMMARY

The following presents a simplified summary in order to provide a basic understanding of some aspects of one or more embodiments or examples of the present invention. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later. Additional goals and advantages will become more evident in the description of the figures, the detailed description of the disclosure, and the claims.

The approach advocated in this application is a portable cost effective approach for diagnosis and monitoring sickle blood activities. The approach, which is explained in greater detail by examples discuss below, are important for a better management of the disease and reducing the medical cost.

An exemplary mobile impedance-based flow cytometer is developed for the diagnosis of sickle cell disease. The mobile cytometer may be controlled by a computer (e.g., smartphone) application. Calibration of the portable device may be performed using a component of known impedance value. With the developed portable flow cytometer, analysis may be performed on both sickle cell samples and healthy cell samples. The acquired results may subsequently be analyzed with a scripting tool (e.g., MATLAB scripts) to extract single-cell level impedance information and/or impedance information of a cell suspension in flow and stationary conditions, as well as statistics of different cell conditions. Significant differences in cell impedance signals may be observed between sickle cells and normal cells, as well as between sickle cells under hypoxia and normoxia conditions.

The portable device may have at least any of three main parts, including for example (i) a customized application, (ii) an impedance reader module, and (iii) a disposable microfluidic chip.

The mobile cytometer's applications include measurement, processing, analysis and logging of electrical impedance data of single particles and a suspension of particles Aided with a computer application (e.g., Android application, iPhone application) developed for this device, users can perform impedance scans over designated lengths of time, graph the measured magnitude and phase of the impedance measured, and share the raw data (e.g., via email, text or other electronic communication) directly from a smartphone.

In an example the impedance reader module serves as an expansion "shield" for a microcontroller (e.g., Arduino UNO) controlled by mobile phone. An impedance converter (e.g., Analog Devices AD5933), wireless switch (e.g., RF switch, Analog Devices HMC245A), transceiver (e.g., wireless transceiver, Bluetooth transceiver, Atomic Market HC-06), in addition to a microSD card adapter, may be connected to the microcontroller on a single printed circuit board. The impedance converter may output a signal with specified voltage amplitude, phase, and frequency depending on commands sent from the microcontroller. The output signal passes through the wireless switch which, with commands from the microcontroller, directs the signal towards either a calibration resistor or an unknown impedance sample placed across a pair of RF connectors (e.g., coaxial connectors, SMA connectors). The signal returns to the impedance converter and impedance measurement are made and collected by the microcontroller. Results may be saved into memory, such as a microSD card.

The microfluidic chip may be disposable and serves as a tool for sampling and creating a single file flow for single particle measurement in a microfluidic channel, or as a sample holder for measurement of a suspension of particles in stationary condition in a microfluidic chamber or channel. The microfluidic chip also controls the particle oxygen environment that can remove oxygen from particles (e.g., sickle cells) using oxygen-poor gases or reducing agents to induced cell sickling and polymerization of hemoglobin variants (HbS, HbC etc.).

The advantage of this device is to provide portability, and affordability to electrical impedance-based flow cytometry as well as a particle suspension in stationary condition, both under a controlled gaseous microenvironment (variant oxygen levels) or equivalent conditions (e.g. reducing agents) that can induce hemoglobin phase transition in hemoglobin variants (HbS, HbC etc.). Measurements can be used to diagnose sickle cell disease and differentiate sickle cell blood samples from sickle cell trait and normal blood. It can measure severity of sickle cell disease. It can also provide a longitudinal measurement from a low sample volume (finger prick) for monitoring the cell sickling events in sickle cell patients.

Exemplary embodiments are described herein. It is envisioned, however, that any system that incorporates features of apparatus and systems described herein are encompassed by the scope and spirit of the exemplary embodiments.

BRIEF DESCRIPTION OF THE DRAWINGS

Various exemplary embodiments of the disclosed apparatuses, mechanisms and methods will be described, in detail, with reference to the following drawings, in which like referenced numerals designate similar or identical elements, and.

DETAILED DESCRIPTION

Figure 1:
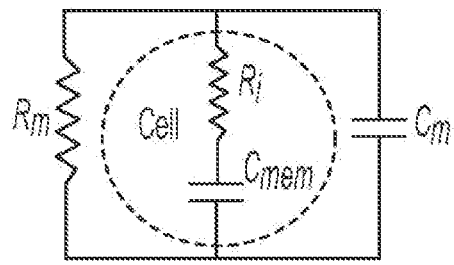
FIG. 1 illustrates an equivalent circuit model of a cell.

Illustrative examples of the devices, systems, and methods disclosed herein are provided below. An embodiment of the devices, systems, and methods may include any one or more, and any combination of, the examples described below. This invention may, however, be embodied in many different forms and should not be construed as limited to the embodiments set forth below. Rather, these exemplary embodiments are provided so that this disclosure will be thorough and complete, and will fully convey the scope of the invention to those skilled in the art. Accordingly, the exemplary embodiments are intended to cover all alternatives, modifications, and equivalents as may be included within the spirit and scope of the apparatuses, mechanisms and methods as described herein.

We initially point out that description of well-known starting materials, processing techniques, components, equipment and other well-known details may merely be summarized or are omitted so as not to unnecessarily obscure the details of the present disclosure. Thus, where details are otherwise well known, we leave it to the application of the present disclosure to suggest or dictate choices relating to those details. The drawings depict various examples related to embodiments of illustrative methods, apparatus, and systems for inking from an inking member to the reimageable surface.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. For example, "a plurality of resistors" may include two or more resistors.

When referring to any numerical range of values herein, such ranges are understood to include each and every number and/or fraction between the stated range minimum and maximum. For example, a range of 0.5-6% would expressly include all intermediate values of 0.6%, 0.7%, and 0.9%, all the way up to and including 5.95%, 5.97%, and 5.99%. The same applies to each other numerical property and/or elemental range set forth herein, unless the context clearly dictates otherwise.

The term "microcontroller" is used herein generally to describe various apparatus relating to the operation of one or more device that directs or regulates a process or machine. A microcontroller is a type of controller and can be implemented in numerous ways (e.g., such as with dedicated hardware) to perform various functions discussed herein. A "microprocessor" is one example of a microcontroller which employs one or more microprocessors that may be programmed using software (e.g., microcode) to perform various functions discussed herein. A microcontroller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs) By example, a microcontroller may include one or more microprocessors, memory and input/output (I/O) peripherals, possibly on a single chip.

The term "electronic switch" refers to an electronic component or device that can switch an electrical circuit, interrupting the current or diverting it from one conductor to another. Typically, electronic switches use solid state devices such as transistors, though vacuum tubes can be used as well in high voltage applications.

The term "transceiver" refers to a device comprising both a transmitter and a receiver that are combined and share common circuitry or a single housing.

The examples present a portable, mobile app controlled impedance-based flow cytometer for diagnosis of blood diseases, such as sickle cell disease. An exemplary application of this cytometer is to measure the impedance of individual red blood cells (RBCs) and differentiate them from sickle cell red blood cells (SRBCs) under induced hypoxia.

The inventors found that electrical impedance of individual red blood cells (RBCs) can be measured to differentiate SRBCs from normal RBCs in a microfluidic device with a cytometer having a small physical size, such as hand held or holdable with a few fingers, and with the ability to directly share acquired data by use of wired or wireless communication (e.g., email, text, etc.) and memory (e.g., portable memory, cloud storage).

Figure 2:
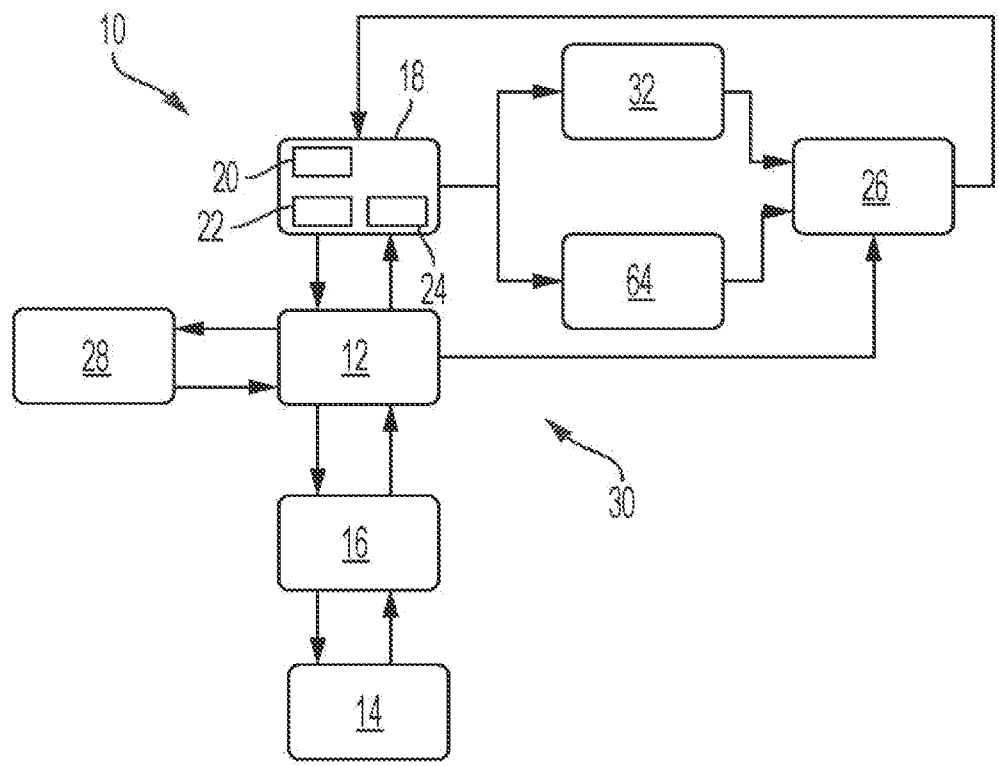
FIG. 2 is a block diagram of a portable impedance-based flow cytometer in accordance with examples of the embodiments.

FIG. 2 depicts an exemplary portable impedance-based flow cytometer 10. A microcontroller 12 (e.g., microprocessor, Arduino UNO) serves as a central component in the cytometer 10, as it collects, processes and relays data between other components of the cytometer. The microcontroller 12 may be programmable, for example, using a variation of C language within the microcontroller compiler. To measure impedance, commands sent from a computer application 14 (e.g., an Android application) may be wirelessly received by a communication device 16 (e.g., HC-06 Bluetooth module) and then sent to the microcontroller 12. In the case of measuring impedance for flow cytometry, computer application commands may be sent from a computer, such as a smartphone, and are eventually processed by the microcontroller 12 via the communication device 16. The microcontroller 12 sends the relevant commands to the impedance converter 18, which generates a sinusoidal signal that is applied to a sample being measured, which may otherwise be referred to as a Device Under Test (DUT). The sample may be for example, a fluid (e.g., blood) or microfluid (e.g., RBCs, SRBCs).

The impedance converter 18 is also known as an impedance-to-digital converter or impedance measuring device that measures the resistance to the flow of alternating current or current at a particular frequency. The impedance converter 18 may be a programmable integrated circuit (IC) that outputs a signal with specified voltage amplitude, phase, and frequency. Impedance of a sample can be then calculated using the voltage and current according to equation (5) above. The impedance converter 18 (e.g., Analog Devices AD5933) may be integrated into a single chip and may include an on-board frequency generator 20 with an analog-to-digital converter 22 (ADC). The frequency generator 20 allows an external complex impedance to be excited with a known frequency, for example, up to 100 kHz. The response signal from the impedance of the sample may be sampled by the on-board ADC 22 and a discrete Fourier transform (DFT) is processed by an on-board digital signal processor (DSP) engine 24. The DFT algorithm may return real (R) and imaginary (I) components at each output frequency allowing calculation of phase and impedance magnitude.

The microcontroller 12 also sends communication signals to an electronically coupled switch 26 (e.g., RF switch, Analog Devices HMC245A) connected to the microcontroller and the impedance converter 18. The RF switch 26 allows the applied signal to return to the impedance converter 18 only after passing through the sample Once the signal returns to the impedance converter 18, the onboard Digital Signal Processor (DSP) engine 24 calculates the impedance of the sample (e.g., RBCc, DUT). Each impedance measurement generated by the impedance converter 18 may be saved in memory 28 (e.g., micro SD card, cache, server, cloud) as collected data. The collected data may be loaded to a connected computer for post-processing, for example through the microcontroller 12 sent wirelessly via the communication device 16 to a computer application 14, such as a smartphone application.

Figure 3:
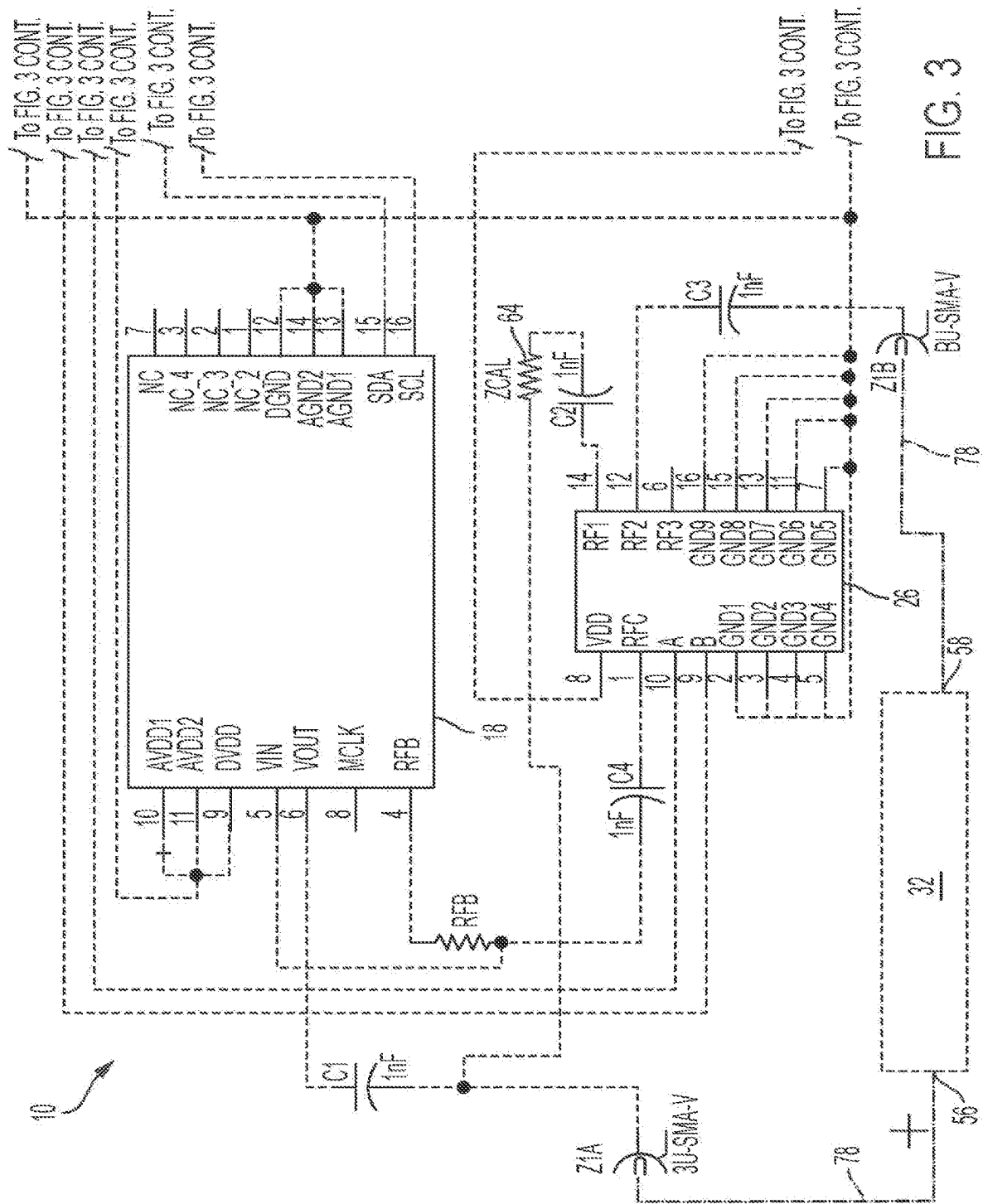
FIG. 3 is a schematic of the exemplary portable impedance-based flow cytometer of FIG. 2.

FIG. 3 is a schematic of the exemplary portable impedance-based flow cytometer 10. The flow cytometer 10 discussed to this point may also be referred to as a portable impedance reader module 30. In other words, the portable impedance reader module 30 includes components such as the microcontroller 12 (e.g., Arduino Uno), communication device 16 (e.g., transceiver, Atomic Market HC-06), impedance converter 18 (e.g., Analog Devices AD5933), electrical switch 26 (e.g., Analog Devices HMC245A), memory 28 (e.g., micro SD) and a calibration resistor 64 discussed in greater detail below. The components may be connected to each other on a printed circuit board (PCB) to compactly house the components. As can be seen in FIGS. 2 and 3, in addition to the portable impedance reader module 30, the cytometer 10 further includes a microfluidic sensor 32 conductively coupled to the impedance converter 18 and the switch 26. The microfluidic sensor 32 may be a disposable chip for sampling and creating a single file flow for single particle impedance measurement in a microfluidic channel, or as a sample holder for impedance measurement of a suspension of particles in stationary condition in a microfluidic chamber or channel. The microfluidic sensor 32 may also control a particle oxygen environment that can remove oxygen from particles (e.g., sickle cells) using oxygen-poor gases or reducing agents (e.g., coating the microfluidic channel) to induced cell sickling and polymerization of hemoglobin variants (HbS, HbC etc.).

Figure 4A:
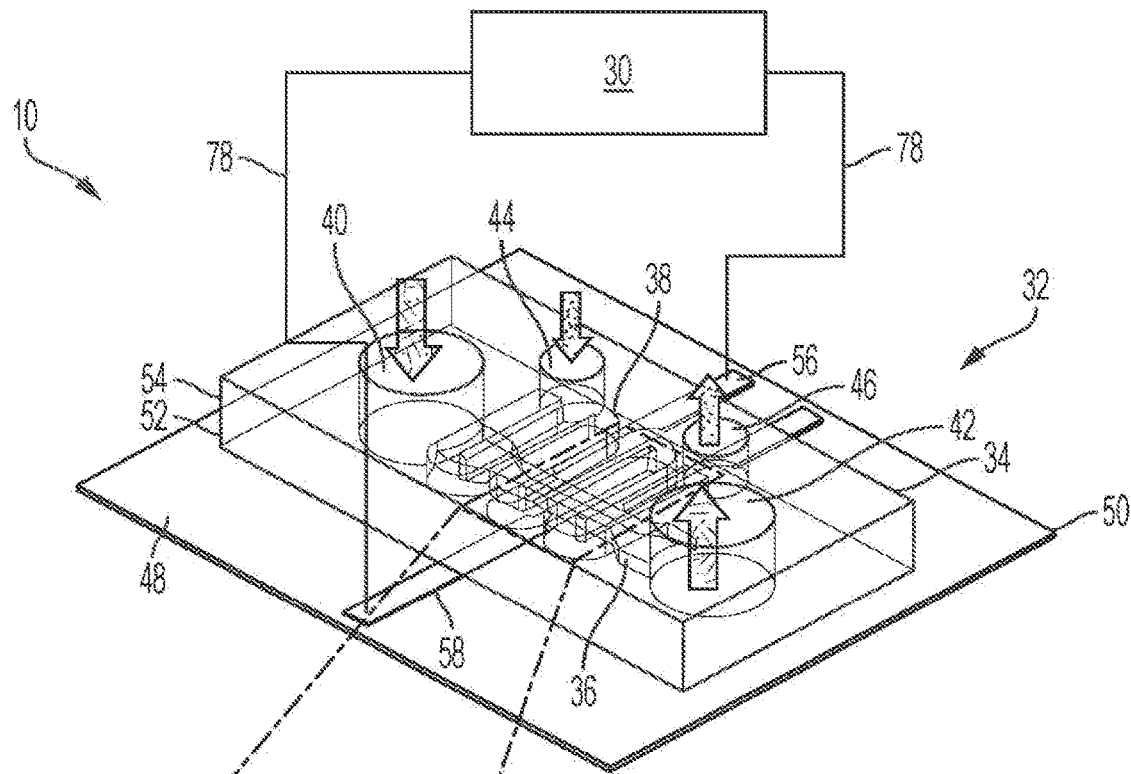
FIG. 4A is a view of an exemplary microfluidic sensor coupled to an exemplary impedance reader module.

FIG. 4A depicts an exemplary microfluidic sensor 32 as a disposable having a channeled portion 34 of material (e.g., glass, silicon, polymer, polydimethylsiloxane (PDMS)) with at least one fluid micro-channel etched or molded into the material. In this example, the channeled portion 34 has a first channel 36 configured to receive a fluid for measurement, and a second channel 38 that may receive a gas. The channels 36, 38 may be micro-channels connected together via fluid communication therebetween to achieve desired features (e.g., fluid mixing, pumping, sorting or otherwise controlling the biochemical environment). The channels 36, 38 formed in the channeled portion 34 of the microfluidic sensor 32 may be accessed from outside the chip via input and output apertures pierced through the chip, as an interface between the macro- and micro-environment. For example, the channel 36 may have a sample input aperture 40 and a sample output aperture 42, and the channel 38 may have a gaseous input aperture 44 and gaseous output aperture 46. It is through these apertures 40, 42, 44, 46 that fluids (e.g., liquids, gases) are injected and removed from the microfluidic sensor 32 (e.g., via tubing, syringe adapters, or the holes in the chip) and interact with external active systems (e.g., pressure controller, push-syringe, peristaltic pump) or passive environments (e.g. hydrostatic pressure).

The channeled portion 34 may be bonded to a flat surface 48 of a substrate 50, such as a glass plate. The channeled portion 34 may have two layers, with a first layer 52 attached (e.g., via adhesive or chemical bonding) to the substrate 50 and including the first channel 36. A second layer 54 above the first layer 52 may have the second channel 38 and access apertures 40, 42, 44, 46 therein for fluid communication between the channels 36, 38 and the macro-environment outside the microfluidic sensor 32.

Electrodes are shown attached to the substrate 50 for communication with at least one of the channels 36, 38 and electronic communication with the cytometer 10 via the impedance converter 18 and switch 26. For example, a first electrode 56 may be connected to an output of the impedance convener 18, and a second electrode 58 may be connected to an input of the RF switch 26. The electrodes are made of a conductive material (e.g., Ti/Au, Au) that retains its conductive properties when exposed to a sample fluid.

As noted above, the microfluidic sensor 32 may be a disposable chip. Accordingly its electrodes 56, 58 are temporarily conductively coupled to the impedance convener 18 and switch 26, respectively Conductive couplers (e.g., metal clips, metal connectors), may be used to connect the electrodes 56, 58 to the impedance converter 18 and switch 26, as well understood by a skilled artisan. Disposable chips may be preferable as the microfluidic sensors 32 to allow replacement of used sensor chips with clean sensor chips having sterile channels 36 for subsequent measurements of different samples.

Figure 4B:
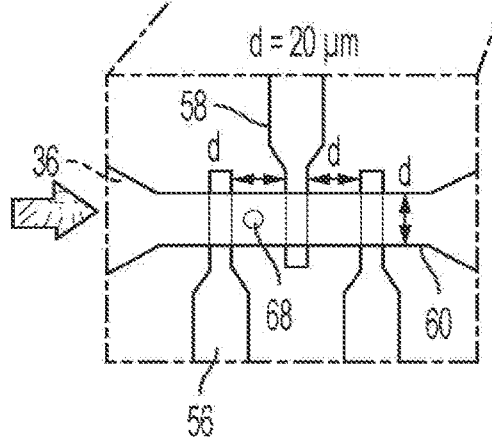
FIG. 4B illustrates exemplary dimensions of a blood cell sample relative to electrodes of a microfluidic sensor.

FIG. 4B illustrates exemplary dimensions of a blood cell sample relative to the electrodes. The electrodes may be, for example, at least 5-50 μm wide, or about 20 μm wide with at least about 5 μm distance "d" (here in this example about 20 μm) between respective electrodes. In addition, the channel 36 may be about 5-80 μm wide (here in this example about 20 μm at a narrowed portion 60 thereof), or at least wide enough to allow at least one single blood cell through the channel for measurement. The channel 36 may be formed using soft lithography as well understood by a skilled artisan. For example, a polymer (e.g., silicone, polydimethylsiloxane) may be used to replicate a mold of the channel from a silicon wafer. When performing an impedance measurement, sample particles may flow through narrow portion 60 of the microfluidic channel 36, which is made narrow to help isolate individual RBCs 62. While not being limited to a particular size, the narrow portion 60 of the channel may measure, for example, about 20 μm wide and about 5 μm deep. These dimensions are for example only, as it is understood that both smaller and larger dimensions are included as within the scope of the invention. At least two of the three electrodes 56, 58, designed 20 μm apart for example, are used for impedance measurement in the example shown in FIG. 4, electrodes 56, 58 were deposited and patterned on a glass substrate 50 using E-beam vaporization and standard microfabrication techniques. The electrodes 56, 58 on the 50 substrate are included as at least part of a microfluidic chip.

Figure 4C:
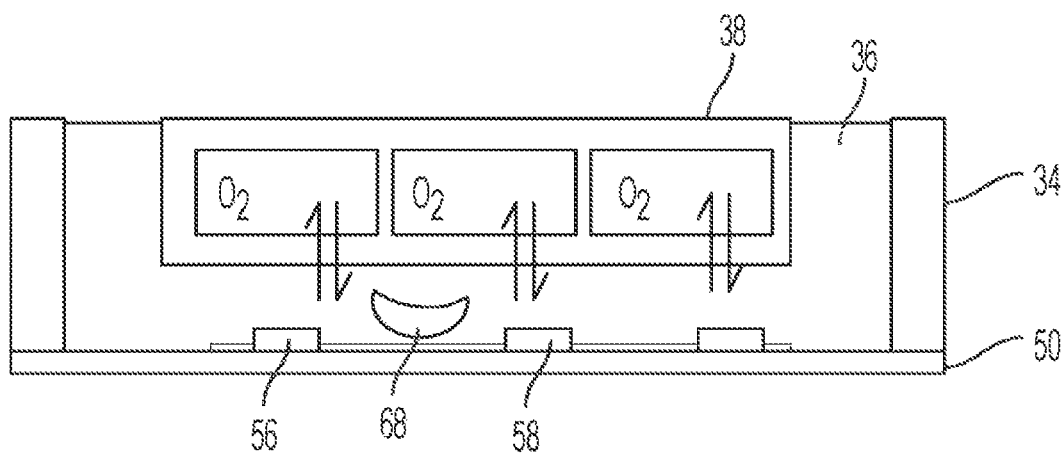
FIG. 4C illustrates a gas exchange in the channeled portion of a microfluidic sensor.

FIG. 4C illustrates a gas (e.g., $O_2$) exchange in the channeled portion from channel 38 that allows sickle cells in the channel 36 to be deoxygenized and exhibit changes in cell shape, as will be discussed in greater detail below. The portable impedance-based flow cytometer 10 may measure single cells of a sample in microfluidic sensor 32 to differentiate SRBCs from normal RBCs, for example, by measuring RBCs under deoxygenated conditions. To produce the deoxygenated environment, the microfluidic sensor 32 may include the double layer channels 36, 38. The structure of the double layer in addition to gas permeable properties of the channel material (e.g., PDMS) allows bottom channel 36 containing RBCs 68 to operate while nitrogen gas is applied to the top channel 38 via gaseous input aperture 44. The applied nitrogen provides a hypoxic deoxygenated environment that forces the SRBCs into sickling.

It should be noted that a deoxygenated environment may also be provided by another example of a microfluidic sensor 32 that may include only one channel 36. In this example, the material of the channeled portion 34 defining the microchannel 36 may be coated with an oxygen depleting chemical (e.g., sodium dithionite (also known as sodium hydrosulfite), sodium metabisulphite, glucose oxidase and catalase), within which the sample flows for impedance measurement thereof. In other words, channel 36 may be transformed to a hypoxic deoxygenated environment by chemical coating of the channel. With chemical coating of the channel 36, the second channel 38 and second layer 54 may not be needed as part of the channeled portion 34 of the sensor 32.

To measure an unknown impedance, the impedance converter 18 should first be calibrated using a known impedance value and known feedback resistor value. While not being limited to a particular theory, the known impedance should be selected to be comparable to the expected range of the impedance to be measured for a proper calibration. The expected range is denoted by defining a minimum, $Z_{min}$, and maximum, $Z_{max}$, expected value. The feedback resistor, $R_{FB}$, can be calculated using the following equation (7) below.

$$R_{FB} = \frac{\left(\frac{V_{DD}}{2} - 0.2\right) \times Z_{min}}{\left(V_{PD} + \frac{V_{DD}}{2} - V_{DCOFFSET}\right)} \times \frac{1}{PGA_{GAIN}} \quad \#(7)$$

where $V_{PK}$ is the peak voltage of the selected output range, $Z_{min}$ is the minimum expected impedance, $PGA_{GAIN}$ is the selected PGA gain, $V_{DD}$ is the supply voltage, and $V_{COFFSET}$ is the DC offset for a selected output range. The calibration resistor 64, $R_{CAL}$, may also be calculated using a value from a predetermined range as shown in equation (8) below where $Z_{max}$ is the maximum expected impedance.

$$R_{CAL} = (Z_{min} + Z_{max}) \times \frac{1}{3} \quad \#(8)$$

The impedance converter 18 is designed to output different signal amplitudes. The inventors understand that the signal-to-noise ratio (SNR) is highest at the largest amplitude, so the impedance converter may be used at its highest amplitude (e.g., about 1.98 volts peak to peak ($V_{p-p}$)). It is understood that the values described are by example only. For example, a supply voltage other than 3.3V changes to the output voltage's amplitude and DC bias by a factor of $V_{CC}$3.3. With a 5V supply, the peak to peak voltage of the output signal at its largest setting is 3 $V_{p-p}$. If the DC level is re-biased, then the following inequality (9) represents the limitation on the impedance range.

$$\frac{Z_{max}}{Z_{min}} \leq 45 \quad \#(9)$$

In order to calibrate and measure an unknown impedance of a sample (e.g., RBC), the portable impedance-based flow cytometer 10 includes switch 26. The switch 26 is implemented to pragmatically switch the path of the signal to pass through either the calibration resistor 64 or the unknown impedance of a sample in the microfluidic sensor 32. While not being limited to a particular structure, the exemplary switch 26 includes two voltage inputs for changing the circuit path to the one containing the calibration impedance. An AC signal from the impedance converter 18 passes through the calibration resistor 64 and returns to the impedance converter 18, where the chip's onboard digital signal processor 24 performs numerous digital signal processing (DSP) techniques and stores the result within data registers on the impedance converter.

The microcontroller 12 may communicate with the impedance converter 18 using a two-wire communication channel also referred to as I²C. Data stored in the impedance converter's registers may represent the admittance of the calibration resistor in the form a+jb. Using equations (2&3) above, the data result can be converted to an impedance magnitude and phase value. This process may be repeated numerous times (e.g., greater than five, fifty or more), and the values may be averaged to obtain a more accurate calibration than could be derived from a single test. The resulting averaged impedance value may then be compared with the known value of the calibration impedance via calibration resistor 64 to calculate a gain factor. Once the gain factor is obtained, a different combination of voltages may be applied to the switch 26 to allow the signal to pass through the unknown impedance sample DUT in the sensor 32. The dimensions of the portable impedance-based flow cytometer 10 allow for easy portability, and may be, for example approximately 7 cm, 5.7 cm, and 7.62 cm in height, width, and length, respectively. The dimensions may also be less than 10 cm in height, width and length, less than 8 cm in height, width and length, less than 15 cm in height, width and length, or other hand holdable distances depending on the size of the components and circuit board.

The computer application 14, which may be software, hardware, firmware, or some combination thereof, may be executed on a small computer, such as a handheld smartphone used in examples, and allows users access via a graphical user interface in communication with smartphone to control the cytometer system. The microcontroller 12 may be programmed via the computer application 14 to optionally read a static impedance value or a time-course measurement during data collection or until the user sends a command to stop data collection.

The graphical user interface (GUI) allows an exemplary smartphone to connect to the communication device 14 of the cytometer 10. The communication device 14 may be intentionally designed to wirelessly transmit and receive serial data between the cytometer 10 and the smartphone. Commands may be transmitted from the smartphone, through the communication device 14 and to the microcontroller 12 which may interpret the commands and initiate appropriate actions in accordance with the commands. For example, the microprocessor 12 may initialize the impedance converter 18 with preset values needed to produce a 1.98 $V_{p-p}$ sinusoidal wave at a frequency of about 100 kHz followed by the application of the appropriate voltages to the RF switch 26 for impedance calibration. The impedance of the known calibration resistor 64 is measured, a gain factor is calculated, and the cytometer 10 is ready to read an unknown impedance sample, for example RBCs 68 in the microfluidic sensor 32.

Figure 5:
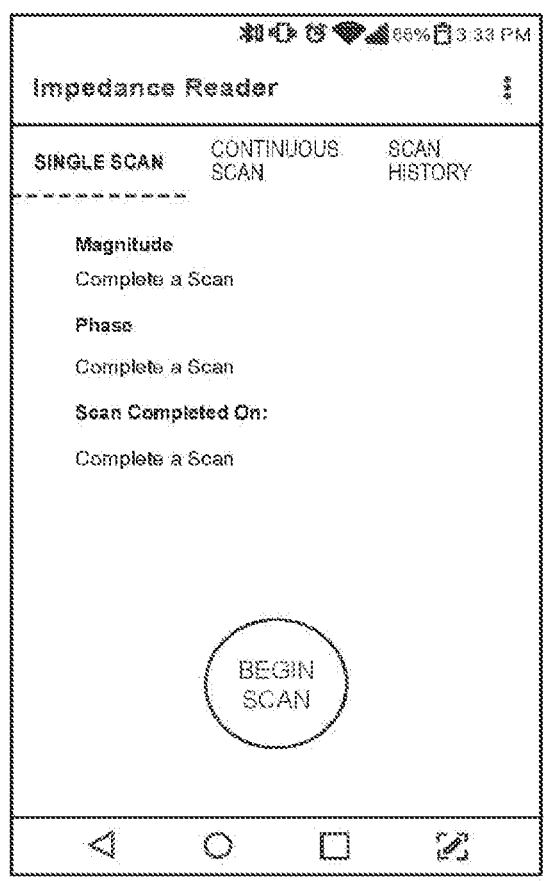
FIG. 5 illustrates a first view of an exemplary GUI.

FIG. 5 depicts an exemplary GUI 70 of an impedance reader system. The GUI 70 may be part of a smartphone 72 (FIG. 10) or in communication with a computer running the computer application 14. As can be seen in FIG. 5, the exemplar GUI 70 shows three tabs with the first two representing two modes of operation. The microcontroller 12 waits for a command issued via wired or wireless communication, for example, over a Bluetooth serial connection between the communication device 16 and the smartphone 72 to initialize one of two impedance scan options. Upon receiving a command, the cytometer 10 may immediately start collecting impedance values for unknown samples, for example, red blood cells in the microfluidic channel 36 using a specified scan method.

One of the scan methods may include a single impedance scan selected in FIG. 5, where results are displayed on the GUI 70 after the scan completes. FIG. 5 shows an initial GUI tab of the application with on-screen options. The most recent single impedance scan result may be stored in the application's memory in or in communication with the computer, and is available for viewing using the option menu in the upper right corner of the GUI 70.

Figure 6:
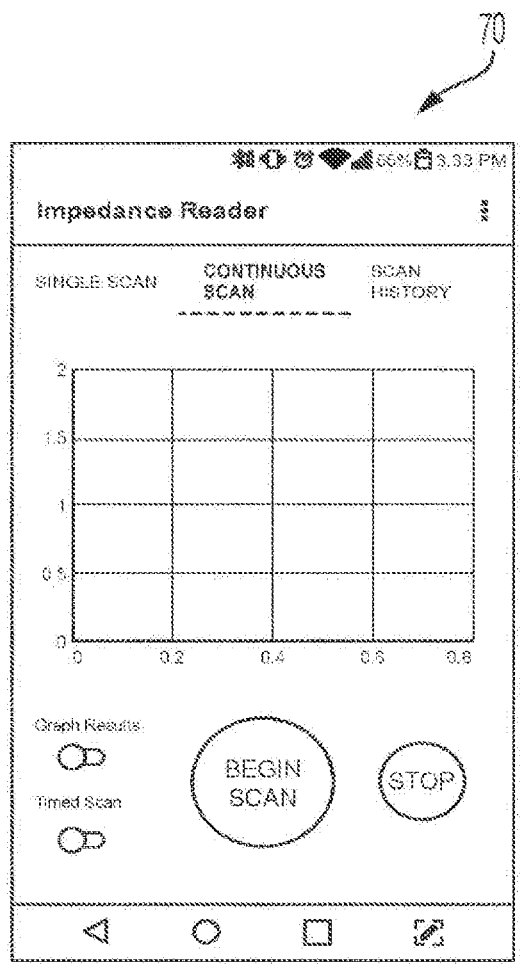
FIG. 6 illustrates a second view of the exemplary GUI.

Another one of the scan methods may include a continuous scan, in this example shown as the second tab. This mode of operation may be preferable for performing flow cytometry. FIG. 6 illustrates an exemplary screenshot of the GIU 70 for this mode. Similar to the single scan tab, both the single scan tab and the continuous scan tab may contain a button labeled "Begin Scan." During a single impedance scan, the "Begin Scan" button is all the user may need to operate the scan. For continuous scanning, users may be presented with an option in the lower left corner for graphing results. Once the continuous scan begins, the cytometer 10 collects data across the electrode terminals 56, 58 for the sample until the user presses the "Stop" button, here shown in the lower right corner of the GUI screenshot. Impedance measurement data may be stored directly onto a microSD card as text file. Optionally, users can choose to graph the impedance measurement results of their continuous scan. If this option is selected in the lower left corner of the screen, data may be transferred from the cytometer 10 to the smartphone 72 (FIG. 10) at the end of the scan. Users can also specify the duration of the scan. For example, when a "Timed Scan" switch is enabled, the user can enter a time in minutes and seconds.

Figure 7:
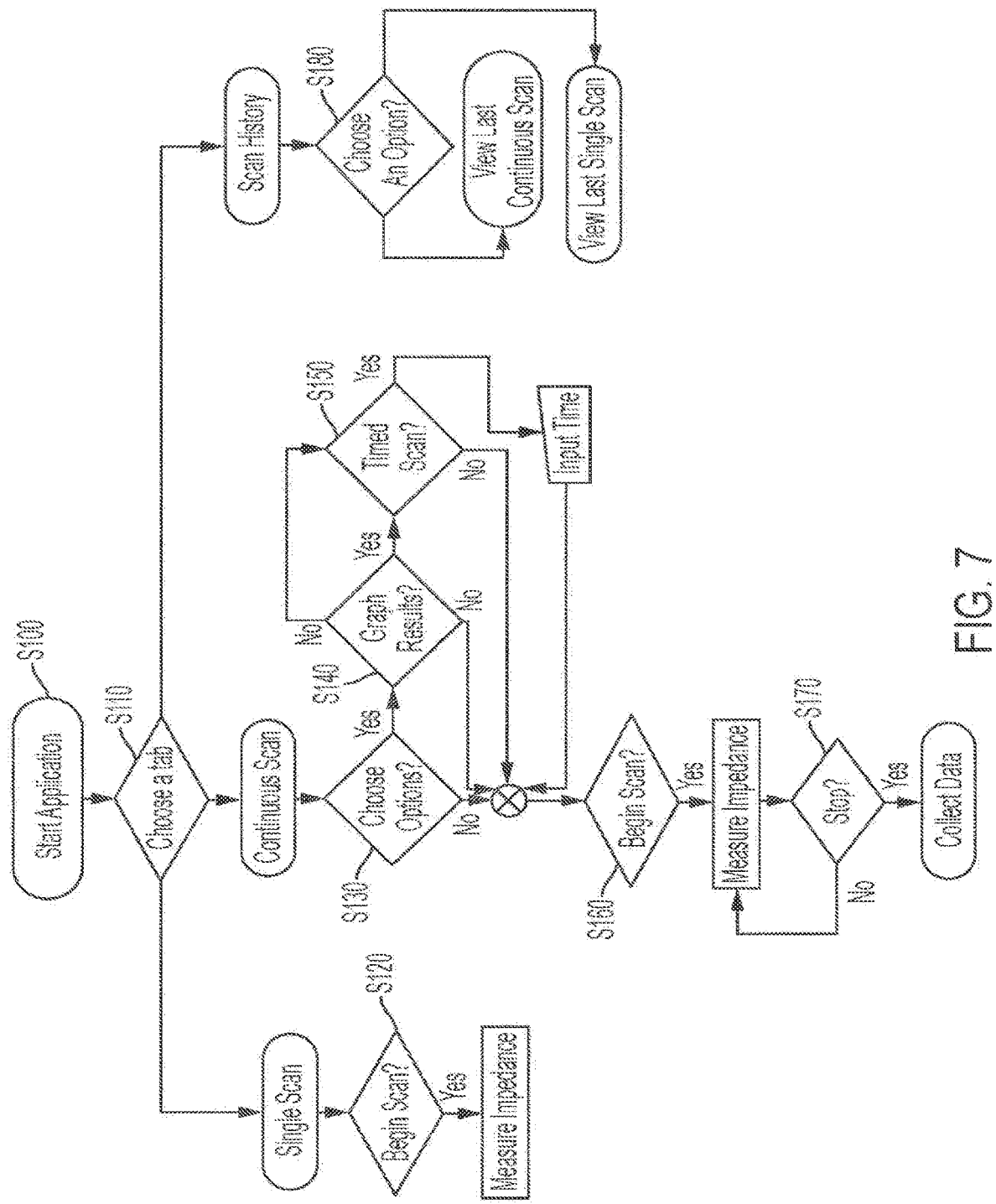
FIG. 7 is a flowchart depicting the operation of a method of an exemplary computer application for measuring impedance of a sample.

The disclosed embodiments may include an exemplary method for operating the computer application 14 on a small computer, such as a smartphone 72 (FIG. 10') FIG. 7 illustrates a flowchart of such an exemplary process flow of the computer application 14 for measuring impedance of a sample, which commences at Step S100 and proceeds to Step S110.

At Step S110, the user may select one of three tabs, for example a single scan tab, a continuous scan tab, and a scan history tab Operation proceeds based on the selection. If a single scan is selected, then operation proceeds to Step S120, whereupon subsequent selection to begin the scan, the application directs the microcontroller 12 to provide a single, averaged value of the impedance's magnitude and phase. Upon completion of the scan and measurement, operation may exit the application or return to the beginning of the application at Step 100.

If a continuous scan is selected at Step S110, then operation proceeds to Step S130, where the user may input options via the GUI. For example, the user may select to receive graph results of the scanned measurements at Step S140, and data acquired by the cytometer during the continuous scan is sent to the computer (e.g., smartphone) and plotted for the user via the GUI. The data may also be saved to the computer's memory or to a remote storage (e.g., remote server memory or accessible memory). As another user input option, if the user selects a timed scan at Step S150, then the user is prompted via the GUI to provide a time limit (e.g., minutes, seconds), and the next continuous scan will automatically end after the designated time elapses.

The continuous scan begins upon subsequent selection at Step S160, where the application directs the cytometer microcontroller to initiate an impedance scan and have each individual data point of measurement continuously stored onto the cytometer's memory (e.g., micro SD card). If no time limit is selected at Step S150, then user selection of an on-screen stop button displayed on the GUI ends the continuous scan at Step S170 and data is collected. The data may be shown via graph format if selected at Step S140, and operation may exit the application or return to the beginning of the application at Step 100.

If scan history is selected at Step S110, then operation proceeds to Step S180, where the GUI allows the user to select an option of the scan history. If the user selects an option to view the last single scan, then the computer GUI displays the results of the most recent single scan. If the user selects an option to view the last continuous scan, then the GUI displays the results of the last continuous scan. Further, the application allows the user to share via email, text or other electronic communication a graph image and numerical data corresponding to the most recent continuous scan that was sent to the computer. Upon completion of the selected scan history, operation may exit the application or return to the beginning of the application at Step 100.

Figure 8:
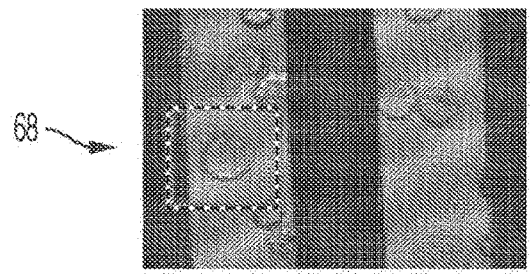
FIG. 8 FIG. 8 illustrates an exemplary appearance of a sickle cell (SRBC) in a normoxia environment.
Figure 9:
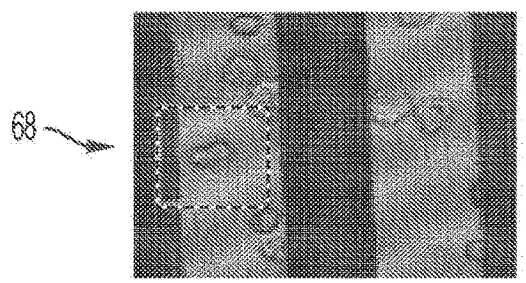
FIG. 9 illustrates an exemplary appearance of a sickle cell (SRBC) in a hypoxia environment.

Under a normoxia condition, RBCs 68 of sickle cell patients take on a classical disc shape as normal RBCs. FIG. 8 illustrates an exemplary appearance of a sickle cell (SRBC) in a normoxia environment as a representation of this disc shape. Under hypoxia, when the oxygen concentration is significantly low, the Hgb S (hemoglobin S, sickle hemoglobin) within a sickle cell polymerizes and the cell changes its shape. FIG. 9 illustrates an exemplary appearance of a sickle cell (SRBC) in a hypoxia environment as a representation of the sickle cell's changed shape. These changes in sickle cells in a hypoxia environment may be identified by changes in impedance measurements of the cells. For example, in comparison to healthy RBCs, sickle cell magnitude, mean phase and standard deviation of the phase exhibit opposite responses in the hypoxia environment. In particular, the presence of sickle cells can be determined if the overall population, under hypoxia, exhibits a decrease in the mean of the cell magnitude, and a decrease in the mean and standard deviation of the phase.

Figure 10:
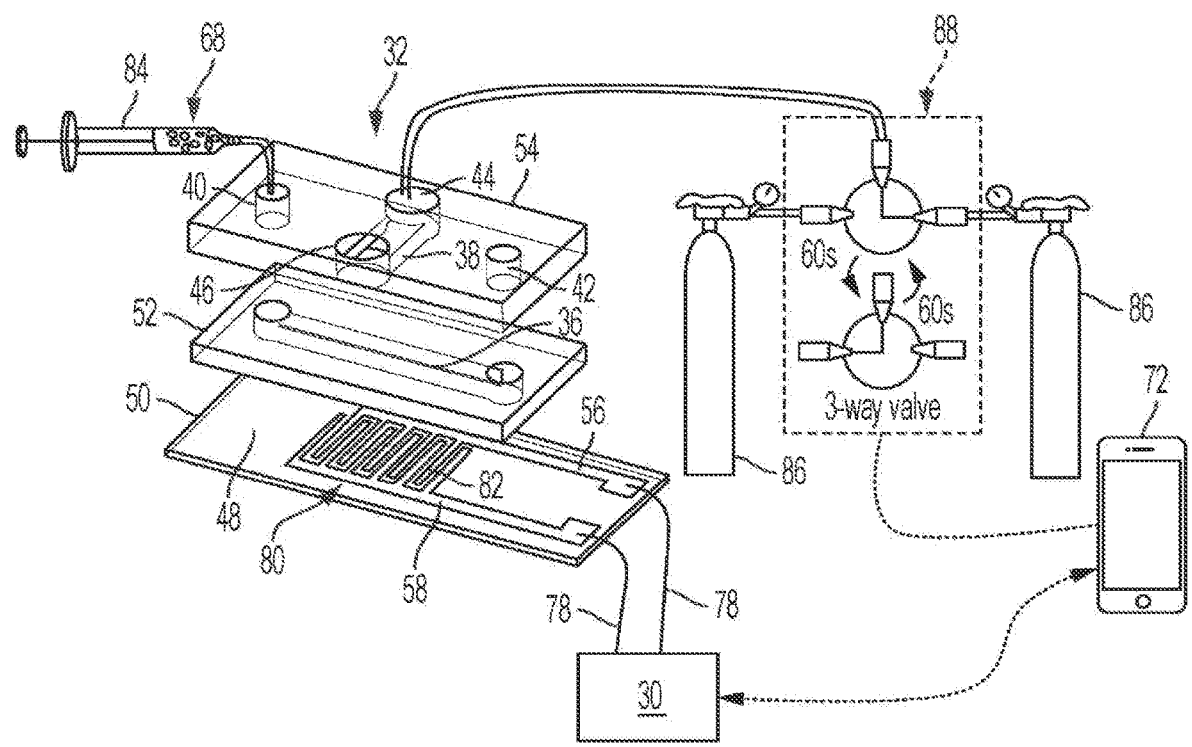
FIG. 10 is a view of another microfluidic sensor in accordance with examples of the embodiments.

FIG. 10 depicts another example of the cytometer 10 with microfluidic impedance sensor 32 in exploded view, with like-referenced numerals designating like parts. As can be seen in FIG. 10, the channeled portion 34 is shown with the first layer 52 including the first channel 36 and the second layer 54 above the first layer 52 and having the second channel 38 and access apertures 40, 42, 44, 46 therein for fluid communication between the channels 36, 38 and the macro-environment outside the microfluidic sensor 32.

The electrodes 56, 58 are shown in FIG. 10 including an interdigitated electrode array 80 that is attached (e.g., printed, adhesively attached, chemical deposition) on a glass substrate. The first channel 36 is shown as a lower cell channel about 500 μm wide and 150 μm deep. The second channel 38 is shown as an upper gas channel about 1500 μm wide and 75 μm deep. A thin silicone layer (e.g., about 150 μm thick PDMS film) may be used to separate the first channel 36 from the second channel 38, allowing gas molecules to permeate through easily while preventing cells from drying out. Access apertures 40, 42, 44, 46 allow separate gas and medium (e.g., sample, RBCs 68) exchanges. The interdigitated electrode array 80 includes a plurality of pairs of fingers 82 (e.g., at least two, at least five, 16 or more). In this example, the fingers 82 may have about 20 μm conductive bands and about 20 μm gaps between adjacent fingers. In this example, fingers 82 may have about a 100-nm-thick Au layer atop a 10-nm-thick Ti layer that are deposited on the substrate 50 (e.g., about 700-μm-thick glass substrate) using E-beam vaporization and patterned by standard photolithography techniques. It should be noted that the dimensions listed above are by example, and dimensions of the fingers 82, substrate 50, and other components of the cyclometer 10 are not limited to those dimensions, but may include larger or smaller dimensions as understood by a skilled artisan.

Microchannels 36, 38 and access apertures 40, 42, 44, 46 may be formed, for example, by casting a microfabricated (e.g., SU-8/Si) master with a degassed silicone (e.g., PDMS) mixture (e.g., 10:1 of base to agent ratio) and curing under heat (e.g., 70° C. for 2 h). A permanent bonding between the first layer 52 and the microchannel and the interdigitated electrode array 80 chip may be accomplished by air plasma treatment. The electrodes 56, 58 may be connected to the portable impedance reader module 30 via conductive wires 78 (e.g., 14-32 gauge copper-based) soldered to the electrodes and connected to the impedance reader module.

Samples of RBCs may be injected gently into the fluid microchannel 36 via access aperture 40 using a syringe 84 (e.g., 0.5 mL or larger). The RBCs may be allowed to sediment to the bottom of the microchannel 36 before impedance measurement is performed.

As can be seen in FIG. 10, oxygen concentration in the microchannel 36 may be controlled by an oxygen concentration in gas mixture supplied to the microchannel 38 from a gas source 86. While discussed above for the purposes of creating a hypoxic deoxygenated environment in the fluid microchannel 36, oxygen concentration control may also be cyclic to evaluate samples under both normoxic and hypoxic conditions. Cyclic hypoxia may be created by switching between an oxygen-rich gas mixture (e.g., 17.5% oxygen, 5% carbon dioxide with the balance of nitrogen) and an oxygen-poor gas mixture (e.g., 5% carbon dioxide with the balance of nitrogen) using a three-way valve 88. The three-way valve 88 may be programmable (e.g., via the computer application 14) or adjusted via human interaction. For example, the three-way valve may switch the gas supply to the microchannel 38 between an oxygen-rich mixture and an oxygen-poor mixture at time intervals as needed for impedance measurement of the sample under desired normoxic and/or hypoxic conditions, for example at time intervals of about 60 seconds.

In an exemplary embodiment of the present invention a computer system may be included and/or operated within which a set of instructions, for causing the machine (e.g., cytometer, smartphone) to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment.

While the machine is discussed in the examples as a smartphone and cytometer, it is understood that the machine may be a personal computer (PC), a tablet PC, a set-top box (STB), a personal digital assistant (PDA), a cellular telephone, a web appliance, a server, a network router, switch or bridge, or any machine capable of executing the computer application 14 or another other set of instructions (sequential or otherwise) that specify actions to be taken by that machine. Further, the term "machine" shall also be taken to include any collection of machines that individually or jointly execute a set (or multiple sets) of instructions to perform any one or more of the methodologies discussed herein.

The exemplary computer system includes a processing device, a main memory (e.g., read-only memory (ROM), flash memory, dynamic random access memory (DRAM) (such as synchronous DRAM (SDRAM) or Rambus DRAM (RDRAM), etc.), a static memory (e.g., flash memory, static random access memory (SRAM), etc.), and a data storage device, which communicate with each other via a bus.

Processing device represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device may also be one or more special-purpose processing devices such as an application specific integrated circuit (ASIC), a field programmable gate array (FPGA), a digital signal processor (DSP), network processor, or the like. Processing device is configured to execute listings manager logic for performing the operations and steps discussed herein.

Computer system may further include a network interface device (e.g., GUI). Computer system also may include a video display unit (e.g., a liquid crystal display (LCD) or a cathode ray tube (CRT)), an alphanumeric input device (e.g., a keyboard), a cursor control device (e.g., a mouse), and a signal generation device (e.g., a speaker).

Data storage device may include a machine-readable storage medium (or more specifically a computer-readable storage medium) having one or more sets of instructions (e.g., reference generation module) embodying any one or more of the methodologies of functions described herein. The reference generation module may also reside, completely or at least partially, within main memory and/or within processing device during execution thereof by computer system; main memory and processing device also constituting machine-readable storage media. The reference generation module may further be transmitted or received over a network via network interface device.

Machine-readable storage medium may also be used to store the device queue manager logic persistently. While a non-transitory machine-readable storage medium is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instruction for execution by the machine and that causes the machine to perform any one or more of the methodologies of the present invention. The term "machine-readable storage medium" shall accordingly be taken to include, but not be limited to, solid-state memories, and optical and magnetic media.

The components and other features described herein can be implemented as discrete hardware components or integrated in the functionality of hardware components such as ASICs, FPGAs, DSPs or similar devices. In addition, these components can be implemented as firmware or functional circuitry within hardware devices. Further, these components can be implemented in any combination of hardware devices and software components.

Some portions of the detailed descriptions are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The instructions may include, for example, computer-executable instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, and the like that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described therein.

In the aforementioned description, numerous details are set forth. It will be apparent, however, to one skilled in the art, that the disclosure may be practiced without these specific details In some instances, well-known structures and devices are shown in block diagram form, rather than in detail, in order to avoid obscuring the disclosure.

The disclosure is related to an apparatus for performing the operations herein. This apparatus may be specially constructed for the required purposes or it may comprise a general purpose computing device selectively activated or reconfigured by a computer program stored therein. Such a computer program may be stored in a non-transitory computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory devices including universal serial bus (USB) storage devices (e.g., USB key devices) or any type of media suitable for storing electronic instructions, each of which may be coupled to a computer system bus.

A portable impedance-based flow cytometer as discussed herein may include, for example, an impedance converter (e.g., Analog Device AD5933 impedance analyzer) to generate and measure the impedance of RBCs passing through a channeled portion with at least one fluid micro-channel bonded to a glass slide coated with gold electrodes. The portable cytometer may be controlled by a computer application, such as an Android application. Commands may be transmitted from the application wirelessly, such as via a serial Bluetooth connection, and received by a communication device of the cytometer. Commands may be processed using the cytometer's microcontroller which also handles the collection and transmission of data. The impedance converter may have only a single output and input so onboard calibration may be achieved using an electronic switch to pass the output signal through a calibration resistor instead of terminals for an unknown impedance. Data collected during impedance scans may be saved to the cytometer's memory (e.g., microSD) and can be optionally transferred to a computer, such as a smartphone over Bluetooth. It is understood that the invention is not limited to the particular microcontroller, impedance converter, switch, calibration resistor, memory, housing (e.g., circuit board), microfluidic device, microfluidic channel, chip, substrate, electrodes, computer, smartphone, and particles identified herein by example.

With the portable impedance-based flow cytometer discussed herein, it is possible to quantify the number of cells that pass through the electrodes and to measure the electrical impedance of single cells. Sickle cells show differences in impedance from healthy cells. These differences may be quantified by the means and standard deviations of the phases of the cells. Therefore, it is possible to differentiate sickle cells from normal cells as well as between different patient conditions with the portable cytometer.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art.

What is claimed is:

1. A system for measuring impedance of particles at a remote location, comprising:
    a microfluidic impedance sensor having a microfluidic channel for sample flow and a microfluidic chip with two electrodes for impedance measurement, the microfluidic channel including an inlet and an outlet, the microfluidic channel housing the impedance sample particles between the inlet and the outlet; and
    a portable impedance-based flow cytometer conductively coupled to the microfluidic impedance sensor, the portable impedance-based flow cytometer having a microcontroller, an impedance converter, a radiofrequency (RF) switch, and a memory, the microcontroller configured to output a command, the impedance converter connected to the microcontroller and configured to output a signal having a voltage amplitude, phase and frequency based on the command output from the microcontroller, the RF switch connected to the microcontroller and the impedance converter, the RF switch configured to receive the signal from the impedance converter, and based on a communication from the microcontroller, direct the signal towards one of a calibration resistor and the impedance sample particles, wherein the signal is modified by the one of the calibration resistor and the impedance sample particles and returned to the impedance converter, the impedance converter further configured to measure the modified signal as impedance data for collection by the microcontroller, the memory in communication with the microcontroller that stores the impedance data, the portable impedance-based flow cytometer further comprising a communication device attached to the microcontroller, the communication device configured for communication with a computer having a graphical user interface, the computer programed with a computer program enabling the computer to connect to the communication device and direct the measuring and monitoring of the impedance data of the particles between the inlet and the outlet of the microfluidic channel.

2. The system of claim 1, further comprising a printed circuit board conductively coupled to the microcontroller, the impedance converter, the RF switch and the memory.

3. The system of claim 1, the microfluidic impedance sensor further including a microfluidic chip with a glass substrate and the two electrodes deposited thereon, the microfluidic channel being defined within a silicone layer bonded with the glass substrate.

4. The system of claim 3, the microfluidic impedance sensor further including a second silicone layer defining a gas chamber having an inlet and an outlet, the inlet being in communication with an oxygen-poor gas mixture source to supply a gas mixture across the microfluidic channel.

5. The system of claim 3, further comprising a chemical coating over the silicone layer defining the microfluidic channel to transform the microfluidic into a hypoxic deoxygenated environment.

6. The system of claim 1, wherein the signal from the impedance converter includes a sinusoidal wave at a frequency of about 100 kHz, the sinusoidal wave being approximately a 1.98 Vp-p sinusoidal wave.

7. The portable impedance-based flow cytometer of claim 1, wherein the portable impedance-based flow cytometer is handheld and weighs less than 1 lb.

8. The portable impedance-based flow cytometer of claim 1, wherein the particles include sickle cell red blood cells.

* * * * *